United States Patent [19]

Clemence et al.

[11] Patent Number: 4,853,408
[45] Date of Patent: * Aug. 1, 1989

[54] 4-PHENYLPROPYL-INDOLES HAVING ANTIARYTHMIC ACTIVITY

[75] Inventors: François Clemence; Jacques Guillaume, both of Paris; Gilles Hamon, Montrouge, all of France

[73] Assignee: Roussel Uclaf, Paris, France

[*] Notice: The portion of the term of this patent subsequent to Mar. 17, 2004 has been disclaimed.

[21] Appl. No.: 853,030

[22] Filed: Apr. 17, 1986

[30] Foreign Application Priority Data

Apr. 23, 1985 [FR] France .................. 85 06135
Jan. 21, 1986 [FR] France .................. 86 00761

[51] Int. Cl.⁴ .................. A61K 31/40; C07D 209/04
[52] U.S. Cl. .................. 514/415; 514/418; 548/469; 548/484; 548/486; 564/347; 564/352; 546/201; 544/373; 544/143
[58] Field of Search .................. 548/469, 484, 486; 514/415, 418; 564/347, 352; 546/201; 544/373, 143

[56] References Cited

U.S. PATENT DOCUMENTS 4,387,100 6/1983 Machin .................. 548/260
4,650,811 3/1987 Guillaume .................. 514/415

FOREIGN PATENT DOCUMENTS 3343671 6/1985 Fed. Rep. of Germany .
730922 6/1955 United Kingdom .................. 564/317

Primary Examiner—Anton H. Sutto
Assistant Examiner—C. H. Cseh
Attorney, Agent, or Firm—Bierman and Muserlian

[57] ABSTRACT

Novel 4-phenylpropyl-indoles of the formula

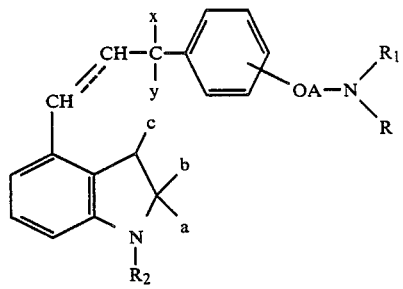

wherein R and $R_1$ are individually selected from the group consisting of hydrogen, linear alkyl of 1 to 5 carbon atoms, branched alkyl of 3 to 5 carbon atoms, cycloalkyl of 3 to 7 carbon atoms cycloalkylalkyl of 4 to 7 carbon atoms and optionally substituted aralkyl of 7 to 12 carbon atoms or $R_1$ and R taken together with the nitrogen atom form an optionally unsaturated heterocycle containing another heteroatom selected from the group consisting of oxygen, sulfur and nitrogen optionally substituted with a member of the group consisting of alkyl of 1 to 5 carbon atoms, phenyl, naphthyl and aralkyl of 7 to 12 carbon atoms, a together with b forms =O or a together with c form a carbon-carbon bond, b is hydrogen or with a forms =O, c is hydrogen or with a forms a carbon-carbon bond, the dotted line is an optional carbon-carbon bond, A is —$(CH_2)_n$—, is an integer from 2 to 5, $R_2$ is selected from the group consisting of hydrogen, linear alkyl of 1 to 5 carbon atoms and branched alkyl of 3 to 5 carbon atoms, x is hydrogen or -OH or together with y forms =O and y is hydrogen or together with x forms =O and their non-toxic, pharmaceutically acceptable acid addition salts having remarkable antiarythmic properties and blocking of slow calcicosodic canals.

18 Claims, No Drawings

4-PHENYLPROPYL-INDOLES HAVING ANTIARYTHMIC ACTIVITY

STATE OF THE ART

Related indoles are described in copending U.S. patent applications Ser. No. 498,835 filed May 27, 1983 and Ser. No. 691,163 filed Jan. 14, 1985, now U.S. Pat. No. 4,650,811 and U.S. Pat. No. 4,333,951 and European Pat. No. 89,426.

OBJECTS OF THE INVENTION

It is an object of the invention to provide the novel 4-phenylpropyl-indoles of formula I and their non-toxic, pharmaceutically acceptable acid addition salts and a novel process for their preparation.

It is another object of the invention to provide novel antiarythmic compositions and to a novel method of inducing anti-arythmic activity in warm-blooded animals.

These and other objects and advantages of the invention will become obvious from the following detailed description.

THE INVENTION

The novel compounds of the invention are selected from the group consisting of 4-phenylpropyl-indoles of the formula

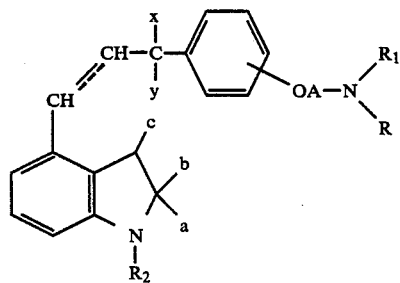

wherein R and $R_1$ are individually selected from the group consisting of hydrogen, linear alkyl of 1 to 5 carbon atoms, branched alkyl of 3 to 5 carbon atoms, cycloalkyl of 3 to 7 carbon atoms, cycloalkylalkyl of 4 to 7 carbon atoms and optionally substituted aralkyl of 7 to 12 carbon atoms or $R_1$ and R taken together with the nitrogen atom form an optionally unsaturated heterocycle containing another heteroatom selected from the group consisting of oxygen, sulfur and nitrogen optionally substituted with a member of the group consisting of alkyl of 1 to 5 carbon atoms, phenyl, napthyl and aralkyl of 7 to 12 carbon atoms, a together with b forms =O or a together with c form a carbon-carbon bond, b is hydrogen or with a forms =O, c is hydrogen or with a forms a carbon-carbon bond, the dotted line is an optional carbon-carbon bond, A is —$(CH_2)_n$—, n is an integer from 2 to 5, $R_2$ is selected from the group consisting of hydrogen, linear alkyl of 1 to 5 carbon atoms and branched alkyl of 3 to 5 carbon atoms, x is hydrogen or —OH or together with y forms =O and y is hydrogen or together with x forms =O and their non-toxic, pharmaceutically acceptable acid addition salts.

In the compounds of formula I, examples of linear and branched alkyl are methyl, ethyl, propyl, isopropyl and tert.-butyl; examples of cycloalkyl of 3 to 7 carbon atoms are cyclopropyl, cyclobutyl, cyclohexyl and preferably cyclopentyl; examples of cycloalkylalkyl are cyclobutylmethyl and preferably cyclopropylmethyl. Examples of aralkyl of 7 to 12 carbon atoms are benzyl and phenethyl optionally substituted with 1 to 3 members of the group consisting of halogen, methyl, ethyl, methoxy, ethoxy, $CF_3$—, $CH_3S$—, —$NH_2$ and —$NO_2$. Examples of heterocycles formed by R and $R_1$ with the nitrogen atom to which they are attached are pyrrolidino, piperidino, morpholino, piperazinyl, methylpiperazinyl, ethylpiperazinyl and propylpiperazinyl.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, arylsulfonic acids such as benzene sulfonic acid or p-toluene sulfonic acid and arylcarboxylic acids such as benzoic acid.

Among the preferred compounds of formula I are those wherein a and c form a double bond and those wherein $R_1$ and $R_2$ are hydrogen and their non-toxic, pharmaceutically acceptable acid addition salts. Examples of specific preferred compounds of formula I are N-[2-{2-(3-[1H-indol-4-yl]-propyl)-phenoxy}-ethyl]-2-methyl-2-propanamine, 1-[2-{3-(1,1-dimethylethylamino)-propoxy}-phenyl]-3-(1H-indol-4-yl)-propanone and N-[2-{2-(3-[1H-indol-4-yl]-propyl)phenoxy}-ethyl]-N-isopropyl-2-propanamine and their non-toxic, pharmaceutically acceptable acid addition salts.

In addition to the compounds set forth in the specific examples infra, other compounds of the following formula are illustrated in the following Table.

| bonding | x | y | O— | n | R | $R_1$ |
|---|---|---|---|---|---|---|
| ⌐ | =O | | 3 | 2 | methyl | methyl |
| ⌐ | =O | | 4 | 2 | " | " |
| ⌐ | =O | | 2 | 3 | " | " |
| ⌐ | =O | | 3 | 3 | " | " |
| ⌐ | =O | | 4 | 3 | " | " |
| — | OH | H | 3 | 2 | " | " |
| — | OH | H | 4 | 2 | " | " |
| — | OH | H | 2 | 3 | " | " |
| — | OH | H | 3 | 3 | methyl | methyl |
| — | OH | H | 4 | 3 | " | " |
| — | H | H | 3 | 2 | " | " |

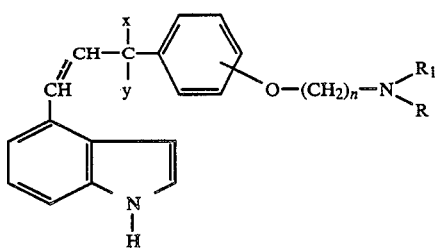

| bonding | x | y | O— | n | R | R₁ |
|---|---|---|---|---|---|---|
| — | H | H | 4 | 2 | " | " |
| — | H | H | 2 | 3 | " | " |
| — | H | H | 3 | 3 | " | " |
| — | H | H | 4 | 3 | " | " |
| — | OH | H | 4 | 2 | t-butyl | H |
| — | H | H | 4 | 2 | " | " |
| ⌒ | OH | H | 4 | 2 | " | " |
| ⌒ | =O | | 3 | 2 | N (piperidine) | |
| ⌒ | =O | | 4 | 2 | " | |
| ⌒ | =O | | 2 | 3 | " | |
| ⌒ | =O | | 3 | 3 | " | |
| ⌒ | =O | | 4 | 3 | " | |
| — | OH | H | 3 | 2 | N (piperidine) | |
| — | OH | H | 4 | 2 | " | |
| — | OH | H | 2 | 3 | " | |
| — | OH | H | 3 | 3 | " | |
| — | OH | H | 4 | 3 | " | |
| — | H | H | 3 | 2 | " | |
| — | H | H | 4 | 2 | " | |
| — | H | H | 2 | 3 | " | |
| — | H | H | 3 | 3 | " | |
| — | H | H | 4 | 3 | " | |
| ⌒ | =O | | 3 | 2 | isopropyl | isopropyl |
| ⌒ | =O | | 4 | 2 | " | " |
| ⌒ | =O | | 2 | 3 | " | " |
| ⌒ | =O | | 3 | 3 | " | " |
| ⌒ | =O | | 4 | 3 | isopropyl | isopropyl |
| — | OH | H | 3 | 2 | " | " |
| — | OH | H | 4 | 2 | " | " |
| — | OH | H | 2 | 3 | " | " |
| — | OH | H | 3 | 3 | " | " |
| — | OH | H | 4 | 3 | " | " |

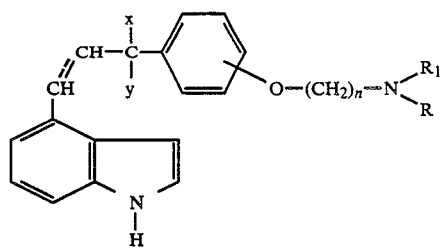

| bonding | x | y | O— | n | R | R₁ |
|---|---|---|---|---|---|---|
| — | H | H | 3 | 2 | " | " |
| — | H | H | 4 | 2 | " | " |
| — | H | H | 2 | 3 | " | " |
| — | H | H | 3 | 3 | isopropyl | isopropyl |
| — | H | H | 4 | 3 | " | " |
| — | =O | | 2 | 2 | propyl | H |
| — | H | H | 2 | 2 | " | H | and their corresponding 2-oxo derivatives.

The novel process of the invention for the preparation of the compounds of formula I and their non-toxic, pharmaceutically acceptable acid addition salts comprises reacting a compound of the formula

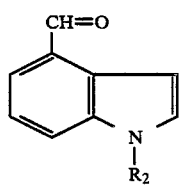

II wherein $R_2$ has the above definition with a compound of the formula

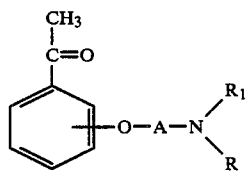

III wherein R, $R_1$ and A have the above definitions to obtain a compound of the formula

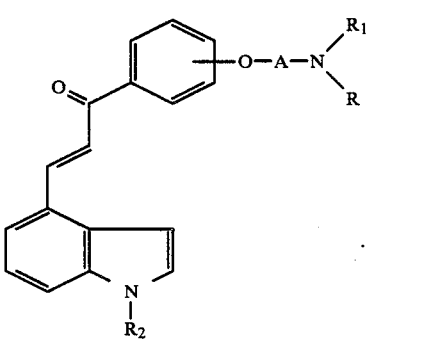

$I_A$ wherein R, $R_1$ and $R_2$ have the above definitions which either is hydrogenated with gaseous hydrogen in the presence of a catalyst based on platinum or palladium in a solvent such as an alkanol of 1 to 5 carbon atoms or with gaseous hydrogen in the presence of Raney nickel in a solvent such as ethyl acetate or reacted with sodium in ammonia for less than 3 hours in a solvent such as tetrahydrofuran to obtain a compound of the formula

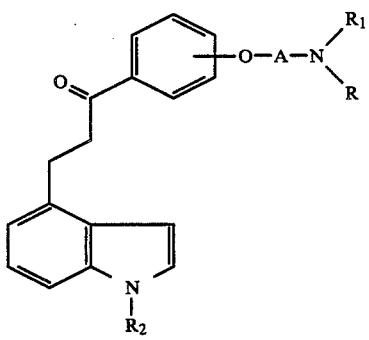

I_B which may be isolated and optionally salified or reducing the same with an alkali metal borohydride or cyanoborohydride to obtain a compound of the formula

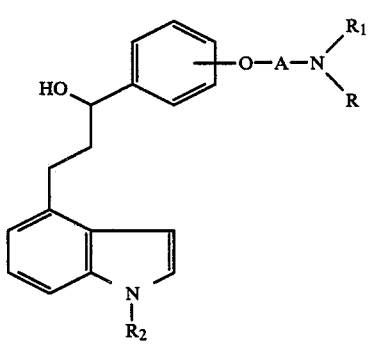

I_C which may be isolated and optionally salified or reducing the latter with sodium in ammonia to obtain a compound of the formula

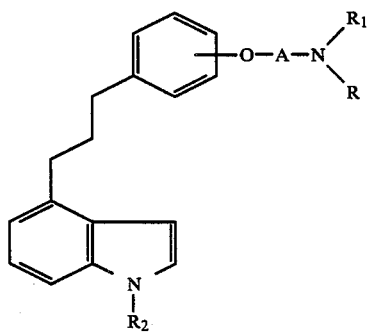

I_D which may be isolated and optionally salified or a compound of formula $I_A$ is reacted with a complex of an alkali metal borohydride and pyridine to obtain a compound of the formula

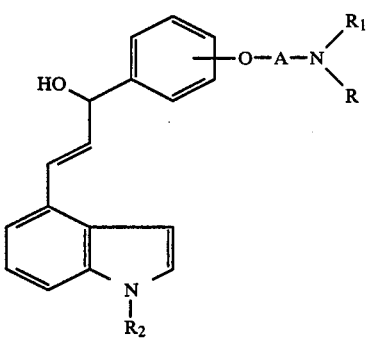

I_E which may be isolated or reduced with sodium in ammonia to obtain a compound of formula $I_D$ which may be isolated and optionally salified or a compound of formula $I_A$ is reduced with sodium in ammonia to obtain a compound of formula $I_D$ which may be isolated and optionally salified or the compounds of formulae $I_A$, $I_B$, $I_C$, $I_D$ and $I_E$ may be reacted with a halogenation agent to obtain a compound of the formula

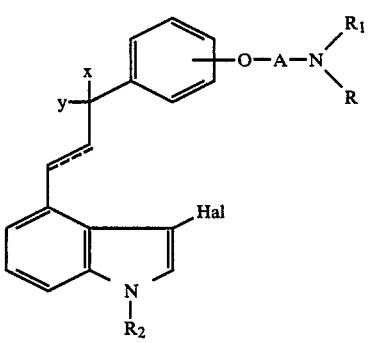

IV wherein Hal is chlorine or bromine which is subjected to hydrolysis to obtain a compound of the formula

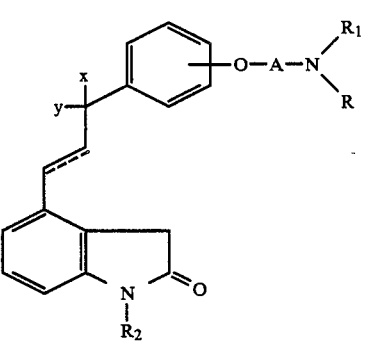

I_F which may be isolated and optionally salified.

The reaction of 4-formyl-indole of formula II with the compound of formula III is preferably effected in the presence of a mineral base such as sodium hydroxide or potassium hydroxide in a solvent such as an alkanol of 1 to 5 carbon atoms, especially ethanol. When the compound of formula $I_B$ is formed from the compound of formula $I_A$ by reaction with sodium in ammonia, the time of reaction is preferably about one hour. To prepare the compound of formula $I_D$, the reaction time is preferably about 6 hours and preferably is in the presence of a solvent such as tetrahydrofuran.

The alkali metal borohydride or cyanoborohydride used to reduce the compounds of formula $I_B$ may be potassium or sodium cyanoborohydride but preferably sodium borohydride is used. The reduction of the compound of formula $I_B$ may also be effected with hydrazine and potassium hydroxide in ethylene glycol. The alkali metal borohydride complexed with pyridine is preferably sodium borohydride and the reaction is preferably effected in an alkanol of 1 to 5 carbon atoms, especially ethanol.

The halogenation of the products of formulae $I_A$, $I_B$, $I_C$, $I_D$ and $I_E$ is preferably effected with a pyridine-bromine complex of the formula

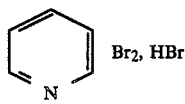

for bromination. Also advantageously used is a N-halosuccinimide such as N-chloro-succinimide or N-bromo-succinimide in dioxane or acetic acid. The product of formula IV is preferably a chlorinated product.

The hydrolysis of the compounds of formula IV is preferably effected with a mineral acid such as phosphoric acid, sulfuric acid and preferably hydrochloric acid in aqueous solution. The acid solution may be concentrated but is preferably dilute such as 1N. One may also use a solvent such as an aliphatic alcohol like ethanol.

A second process for the preparation of the compounds of formula I and their acid addition salts comprises reacting a compound of the formula

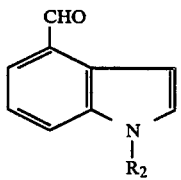

II wherein $R_2$ has the above definition with a compound of the formula

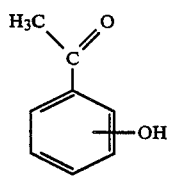

III' to obtain a compound of the formula

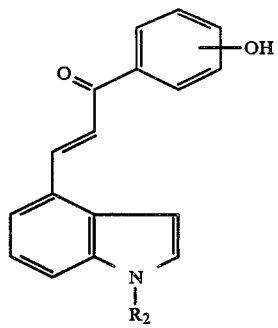

IX which either is hydrogenated with gaseous hydrogen in the presence of a catalyst based on platinum or palladium in a solvent such as an alkanol of 1 to 5 carbon atoms or with gaseous hydrogen in the presence of Raney nickel in a solvent such as ethyl acetate or reacted with sodium in ammonia for less than 3 hours in a solvent such as tetrahydrofuran to obtain a compound of the formula

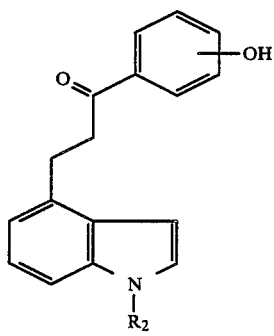

X which is reduced with an alkali metal borohydride or cyanoborohydride to obtain a compound of the formula

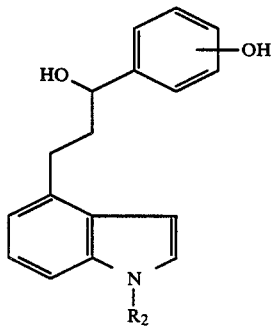

XI reducing the latter with sodium in ammonia to obtain a compound of the formula

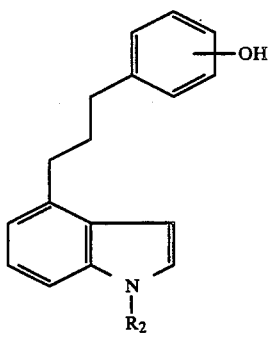

XII or reducing the compound of formula IX with a complex of pyridine and an alkali metal borohydride to obtain a compound of the formula

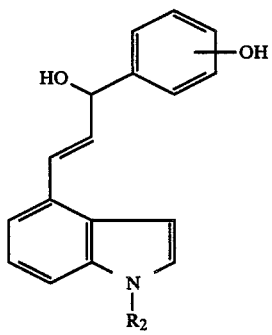

XIII reducing the latter with sodium in ammonia to obtain a compound of formula XII or reducing a compound of formula IX with sodium in ammonia to obtain a product of formula XII or reducing a compound of formula X with hydrazine and potassium hydroxide in ethylene glycol to obtain a compound of formula XII and, if desired, the compounds of formulae IX, X, XI, XII and XIII may be reacted with a halogenation agent to obtain a compound of the formula

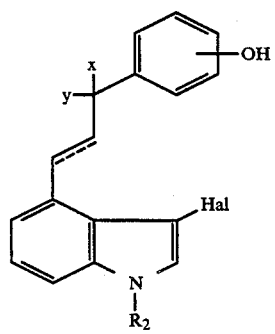

XIV wherein Hal is chlorine or bromine which is subjected to hydrolysis to obtain a compound of the formula

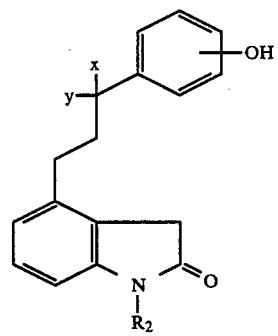

XV then reacting a compound of formulae IX, X, XI, XII, XIII or XV with a halide of the formula

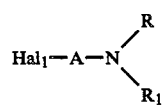

XVI wherein $Hal_1$ is chlorine, bromine or iodine to obtain a compound of the formula

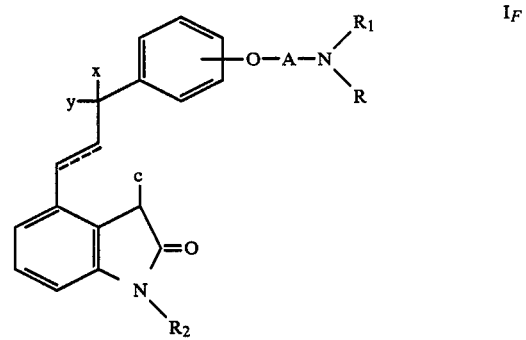

$I_F$ which may be isolated and optionally salified.

The reaction of the compounds of formulae II and III' is effected in the same manner as the compounds of formulae II and III. When one prepares a product of formula X or XII, the same procedures as the preparation of the compounds of formula $I_B$ or $I_D$ are used. The alkali metal borohydride or cyanoborohydride used to reduce the compounds of formula X may be sodium or potassium cyanoborohydride or preferably sodium borohydride and hydrazine may be used in the form of its hydrate in the presence of potassium hydroxide and ethylene glycol.

The alkali metal borohydride complexed with pyridine is preferably sodium borohydride and reaction is preferably effected in an alkanol of 1 to 5 carbon atoms such as ethanol. The halogenation of the compounds of formulae IX, X, XI, XII and XIII may be effected as above for the compounds of formulae $I_A$, $I_B$, $I_C$, $I_D$ and $I_E$. The compounds of formulae XIV is preferably chlorinated and the hydrolysis is effected as with the compounds of formula IV.

The reaction of the compounds of formulae XV and XVI is effected in a phase transfer reaction preferably using as the aqueous phase an aqueous alkali metal hydroxide such as sodium hydroxide and as the organic phase a water-immiscible organic solvent such as benzene in the presence of a phase transfer agent such as preferably tetrabutylammonium hydrogen sulfate or bromide.

The compounds of formula II are known and may be prepared by the process of J. Org. Chem., Vol. 45 (1980), p. 3350, for example. The compounds of formula III' are also known. The compounds of formula III are known and may be prepared by the process described in Helv. Chim. Acta., Vol. 46, (1963), p. 1696 to 1704. They may be prepared by a phase transfer reaction with a phenol of the formula

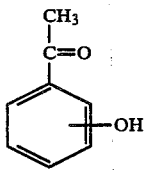

V or a ω-chloroalkyl p-toluene sulfonate using as the aqueous phase aqueous alkali metal hydroxide such as sodium hydroxide and as the organic phase a water-immiscible organic solvent such as benzene in the presence of a phase transfer catalyst such as tetrabutylammonium bromide or hydrogensulfate or an α-bromo-ω-chloro-alkylene, preferably in the presence of a condensation agent like a base such as an alkali metal carbonate or bicarbonate to obtain a compound of the formula

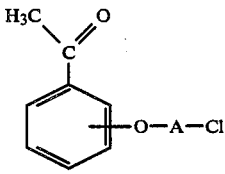

VI reacting the latter with an amine of the formula $R_1$—NH—R  VII wherein R and $R_1$ have the above definition except they are not both hydrogen in a solvent preferably in the presence of a condensation agent such as an alkali metal carbonate or using the amine as solvent.

To obtain a compound of formula III wherein R and $R_1$ are both hydrogen, a compound of formula V is reacted with a nitrile of the formula Cl—A'—CN  VIII wherein A' is the lower homolog of A preferably in the presence of a condensation agent and the resulting product is subjected to catalytic hydrogenation, preferably in the presence of Raney nickel.

The compounds of formula I have a basic character and the acid addition salts can be easily prepared by reaction of stoichiometric amounts of the acid and compound of formula I with or without isolation of the free base.

The novel anti-arythmic compositions of the invention are comprised of an anti-arythmically effective amount of at least one compound of formula I and their non-toxic, pharmaceutically acceptable acid addition salts and an inert pharmaceutical carrier or excipient. The compositions also possess properties of blocking the slow calcicosodic canals and certain of the compounds of formula I possess anti-serotoninergic properties. The compositions may be in the form of tablets, dragees, gelules, capsules, granules, suppositories and injectable solutions or suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The compositions are useful for the treatment of cardiac insufficiency, all forms of angor and for the treatment of arythmia. Certain compounds are also useful for the treatment of spasms. The antiserotoninergic activity can be seen by pharmological tests such as inhibition of bronchospasms of serotonine.

Among the preferred compositions of the invention are those wherein in the active compound a and c form a double bond and those wherein in the active compound $R_1$ and $R_2$ are hydrogen and their non-toxic, pharmaceutically acceptable acid addition salts. Specific referred compositions are those wherein the active ingredient is selected from the group consisting of N-[2-{2-(3-[1H-indol-4-yl]-propyl)-phenoxy}-ethyl]-2-methyl-2-propanamine, 1-[2-{3-(1,1-dimethylethylamino)-propoxy}-phenyl]-3-(1H-indol-4-yl)-propanone and N-[2-{2-(3-[1H-indol-4-yl]-propyl)-phenoxy}-ethyl]-N-isopropyl-2-propanamine and their non-toxic, pharmaceutically acceptable acid addition salts.

The novel method of the invention for inducing anti-arythmic activity in warm-blooded animals, including humans, comprises administering to warm-blooded animals an anti-arythmically effective amount of at least one compound of formula I and their non-toxic, pharmaceutically acceptable acid addition salts. The compounds may be administered orally, rectally or parenterally and the usual daily dose is 0.65 to 13 mg/kg depending on the compound, method of administration and condition treated. For example, the compounds of Example 4 and 24 may be administered orally at a dose of 3 to 12 mg/kg for treatment of ventricular, supraventricular and junction arythmia.

In the following examples there are described several preferred embodiments to illustrate the invention. However, it should be understood that the invention is not intended to be limited to the specific embodiments.

EXAMPLE 1

1-[2-{2-(1,1-dimethylethylamino)-ethoxy}-phenyl]-3-[1H-indol-4-yl]-2-propen-1-one (E)

A solution of 5.4 g of 1-[2-{2-(1,1-dimethylethylamino)-ethoxy}-phenyl]-ethanone in 75 ml of ethanol was added with stirring under an inert atmosphere to a mixture of 3.339 g of indole-4-carboxaldehyde and 6 ml of 50% sodium hydroxide solution and after stirring for 4 hours, the mixture was diluted with water and extracted with ethyl acetate. The organic phase was washed with aqueous sodium chloride solution, dried over a deshydrant and evaporated to dryness under reduced pressure. The residue was chromatographed over silica and eluted with a 9-1 ethyl acetate-triethylamine mixture to obtain 7.41 g of 1-[2-{2-(1,1-dimethylethylamino)-ethoxy}-phenyl]-3-[1H-indol-4-yl]-2-propen-1-one (E).

1.24 g of DL tartaric acid were added with stirring at 80° C. to a solution of 3 g of the said base in 150 ml of isopropanol and 50 ml of methanol and the mixture was held at 80° C. for 20 minutes and was then evaporated to dryness. The residue was taken up in 45 ml of methanol and 50 ml of isopropanol containing a little pentane and after crystallization, the mixture was filtered. The product was dried at 80° C. under reduced pressure to obtain in two crops 2.83 g of (+)2,3-dihydroxybutanedioate acid salt of the base melting at 172° C.

Analysis (first crop): $C_{23}H_{26}N_2O_2.C_4H_6O_6$; molecular weight=512.564. Calculated: %C 63.27, %H 6.29, %N 5.46. Found: %C 63.3, %H 6.6, %N 5.5.

EXAMPLE 2

1-[2-{2-(1,1-dimethylethylamino)-ethoxy}-phenyl]-3-[1H-indol-4-yl]-1-propanone

A mixture of 3.218 g of the free base of Example 1, 1.1 g of 10% palladized carbon and 350 ml of methanol was hydrogenated with stirring and was then filtered. The filtrate was evaporated to dryness under reduced pressure and the residue was washed with 7 ml of isopropanol and filtered. The product was dried under reduced pressure to obtain 2.35 g of 1-[2-{2-(1,1-dimethylethylamino)-ethoxy}-phenyl]-3-[1H-indol-4-yl]-1-propanone melting at ≃112° C.

4 ml of a solution of hydrogen chloride in ethyl acetate were added to a suspension of 2.25 g of the said base in 70 ml of isopropanol and the mixture was filtered. The product was dried at 80° C. to obtain 2.38 g of the hydrochloride of the base melting at ≃250° C.

Analysis: $C_{23}H_{28}N_2O_2.HCl$; molecular weight=400.952. Calculated: %C 68.9, %H 7.29, %N 6.99, %Cl 8.84. Found: %C 68.9, %H 7.5, %N 6.9, %Cl 8.7.

EXAMPLE 3

α-[2-{2-(1,1-dimethylethylamino)-ethoxy}-phenyl]-1H-indole-4-propanol 0.934 g of sodium borohydride were added to a solution of 3 g of the free base of Example 2 in 90 ml of methanol and after stirring for 20 minutes under an inert atmosphere, iced water was added thereto. The mixture was extracted with ethyl acetate and the organic phase was washed with water, dried over a deshydrant and evaporated to dryness to obtain 2.79 g of α-[2-{2-(1,1-dimethylethylamino)-ethoxy}-phenyl]-1H-indole-4-propanol.

0.862 g of fumaric acid were added with stirring to a solution of 2.73 g of the above base in 70 ml of isopropanol and then another 20 ml of isopropanol were added. Crystallization was induced and after standing 16 hours at 4° C., the mixture was filtered. The product was dried at 80° C. under reduced pressure to obtain 2.5 g of the neutral (E) butenedioate salt of the free base melting at ≃190° C.

Analysis: $(C_{23}H_{30}N_2O_2)_2.C_4H_4O_4$: molecular weight=849.089. Calculated: %C 70.73, %H 7.60, %N 6.60. Found: %C 70.5, %H 7.8, %N 6.5.

EXAMPLE 4

N-[2-{2-(3-[1H-indol-4-yl]-propyl)-phenoxy}-ethyl]-2-methyl-2-propanamine 3 ml of ammonia at −78° C. were added to a solution of 31 mg of the free base of Example 3 in 2 ml of tetrahydrofuran and 100 mg of sodium were added under an inert atmosphere at −40° C. After stirring for one hour, 800 mg of ammonium chloride were added at −40° C. and the mixture was allowed to evaporate at room temperature. Water was added and the mixture was extracted with ethyl acetate. The organic phase was washed with water, aqueous sodium chloride, dried over a deshydrant, filtered and evaporated to dryness. A little pentane was added to the residue and the mixture was filtered. The product was dried to obtain 22 mg of N-[2-{2-(3-[1H-indol-4-yl]-propyl)-phenoxy}-ethyl]-2-methyl-2-propanamine melting at ≃112° C.

EXAMPLE 5

1-[2-{3-(1,1-dimethylethylamino)-propoxy}-phenyl]-3-[1H-indol-4-yl]-2-propen-1-one STEP A: 1-[2-{3-chloropropoxy}-phenyl]-ethanone 2 ml of 2-hydroxy-acetophenone were added with stirring to a mixture of 2.31 g of tetrabutylammonium acid sulfate, 20 ml of 50% sodium hydroxide solution, 40 ml of benzene and 20 ml of acetonitrile and after adding 8.26 of 3-chloro-propyl p-toluene sulfonate, the mixture was heated under an inert atmosphere at 80° C. for 17 hours. The decanted aqueous phase was extracted with benzene and the organic phase was washed with water, dried over a deshydrant, filtered and evaporated to dryness. The residue was chromatographed over silica and eluted with a 95-5 benzene-ethyl acetate mixture. Evaporation of the solvents yielded 3.38 g of 1-[2-{3-chloropropoxy}-phenyl]-ethanone.

STEP B:
1-[2-{3-(1,1-dimethylethylamino)-propoxy}-phenyl]-ethanone

A mixture of 2.58 g of the product of Step A, 8.3 ml of tert.-butylamine and 2.17 g of potassium carbonate in 7 ml of N,N-dimethylformamide was heated with stirring at 120° C. for 19 hours and was then diluted with water. The mixture was extracted with ethyl acetate and the organic phase was washed with water, dried over a deshydrant and evaporated to dryness under reduced pressure. The residue was chromatographed over silica and eluted with a 9-1 ethyl acetate-triethylamine mixture to obtain 2.571 g of 1-[2-{3-(1,1-dimethylethylamino)-propoxy}-phenyl]-ethanone.

STEP C:
1-[2-{3-(1,1-dimethylamino)-propoxy}-phenyl]-3-[1H-indol-4-yl]-2-propen-1-one 3 ml of 50% sodium hydroxide solution and then 1.484 g of indole-4-carboxaldehyde were added to a solution of 2.55 g of 1-[2-{3-(1,1-dimethylethylamino)-propoxy}-phenyl]-ethanone in 35 ml of ethanol and the mixture was stirred under an inert atmosphere for 20 minutes. The mixture was diluted with water and extracted with ethyl acetate. The organic phase was washed with water, dried over a deshydrant, filtered and evaporated to dryness under reduced pressure. The residue was chromatographed over silica and eluted with a 9-1 ethyl acetate-triethylamine mixture to obtain 2.804 g of 1-[2-{3-(1,1-dimethylethylamino)-propoxy}-phenyl]-3-[1H-indol-4-yl]-2-propen-1-one.

1.065 g of DL tartaric acid were added to a solution of 2.672 g of the said base in 70 ml of isopropanol at 80° C. and the mixture stood at 80° C. for 25 minutes and was then dried. The residue was empasted with pentane and then a mixture of methanol and isopropanol was added. The mixture was filtered and dried at 80° C. under reduced pressure to obtain in 2 crops 2.319 g of acid (+) 2,3-dihydroxy-butanedioate salt of the base melting at ≃184° C.

Analysis: $C_{24}H_{28}N_2O_2.C_4H_6O_6$; molecular weight=526.591. Calculated: %C 63.86, %H 6.51, %N 5.32. Found: %C 63.7, %H 6.7, %N 5.4.

EXAMPLE 6

1-[2-{3-(1,1-dimethylethylamino)-propoxy}-phenyl]-3-[1H-indol-4-yl]-2-propen-1-ol A mixture of 4.38 g of the free base of Example 5, 1.76 g of sodium borohydride and 3.4 ml of pyridine and 85 ml of methanol was heated at 70° C. for 15 minutes and was diluted with water with cooling in an ice bath. The mixture was extracted with ethyl acetate and the organic phase was washed with water, with aqueous sodium chloride, dried over a deshydrant, filtered and evaporated to dryness under reduced pressure. Pentane was added to the residue and the mixture was filtered. The product was washed with isopropanol and dried under reduced pressure to obtain 2.576 g of 1-[2-{3-(1,1-dimethylethylamino)-propoxy}-phenyl]-3-[1H-indol-4-yl]-2-propen-1-ol melting at ≃140° C.

EXAMPLE 7

N-[3-{2-(3-[1H-indol-4yl]-propyl)-phenoxy}-propyl]-2-methyl-2-propanamine

A solution of 3.38 g of the product of Example 6 and 25 ml of tetrahydrofuran was added at −78° C. to 30 ml of ammonia and after adding 3 g of sodiunm at −40° C., the mixture was stirred for 90 minutes under an inert atmosphere. 24 g of ammonium chloride were added at −40° C. and the ammonia evaporated. The residue was diluted with water and the mixture was extracted with ethyl acetate. The organic phase was washed with water, aqueous sodium chloride, dried over a deshydrant, filtered and evaporated to dryness to obtain 2.86 g of N-[3-{2-(3-[1H-indol-4-yl]-propyl)-phenoxy}-propyl]2-methyl-2-propanamine.

A solution of 0.898 g of fumaric acid in 60 ml of hot acetone was added to a solution of 2.82 g of the said base in 30 ml of acetone and the mixture was filtered, washed with isopropanol and evaporated to dryness under reduced pressure. The residue was taken up in 100 ml of ethanol with heating and was filtered. The product was dried at 80° C. under reduced pressure to obtain 2.165 g of the neutral (E) butanedioate of the said base melting at ≃230° C.

Analysis: $C_{24}H_{32}N_2O.\frac{1}{2}(C_4H_4O_4)$; molecular weight=422.572. Calculated %C 73.90, %H 8.11, %N 6.63. Found: %C 69.98, %H 7.55, %N 5.83.

EXAMPLE 8

1-[2-{2-(1,1-dimethylethylamino)-ethoxy}-phenyl]-3-[1H-indol-4-yl]-2-propen-1-ol 1.1 ml of pyridine and 624 mg of sodium borohydride were added under an inert atmosphere to a solution of 1.5 g of the base of Example 1 and 35 ml of ethanol and after stirring at 70° C. for 15 minutes, water was added thereto. The mixture was cooled in an ice bath and was extracted with ethyl acetate. The organic phase was washed with water, dried over a deshydrant and evaporated to dryness. The residue was chromatographed over silica and eluted with a 9-1 ethyl acetate-triethylamine mixture to obtain 1.32 g of 1-[2{-2-(1,1-dimethylethylamino)-ethoxy}-phenyl]-3-[1H-indol-4-yl]-2-propen-1-ol.

UV Spectrum (ethanol):

| Max. at 221 nm | $E_1^1 = 685$ | $\epsilon = 24{,}968$ |
| Inflex towards 233 nm | $E_1^1 = 533$ | |
| Inflex towards 276 nm | $E_1^1 = 151$ | |
| Inflex towards 285 nm | $E_1^1 = 186$ | |
| Inflex towards 292 nm | $E_1^1 = 219$ | |
| Max. at 308 nm | $E_1^1 = 267$ | $\epsilon = 9{,}732$ |

EXAMPLE 9

N-[2-{2-(3-[1H-indol-4-yl]-propyl)-phenoxy}-ethyl]-2-propanamine

A solution of 3.936 g of the base of Example 8 in 25 ml of tetrahydrofran was added at −78° C. to 30 ml of liquid ammonia and 4.2 g of pieces of sodium were added at −40° C. followed by stirring under an inert atmosphere for two hours. 36 g of ammonium chloride were added at −40° C. and the ammonia was allowed to evaported. The residue was diluted with water while cooling in an ice bath and was extracted with ethyl acetate. The organic phase was washed with water, dried over deshydrant, filtered and evaporated to dryness. The residue was washed with isopropanol and dried under reduced pressure to obtain 2.43 g of N-[2-{2-(3-[1H-indol-4-yl]-propyl)-phenoxy}-ethyl]-2-methyl-2-propanamine melting at 114° C.

A solution of 2.4 g of the said base in 90 ml of ethanol was added with stirring to 0.795 g of fumaric acid and the mixture was concentrated and seeded to induce crystallization. The mixture stood at 4° C. for 16 hours, was filtered and dried under reduced pressure to obtain 1.67 g of the neutral (E) butanedioate salt melting at ≃190° C.

Analysis: $C_{23}H_{30}N_2O.\frac{1}{2}(C_4H_4O_4)$; molecular weight=408.545. Calculated: %C 73.50, %H 7.89, %N 6.86. Found: %C 73.3, %H 7.9, %N 7.2.

EXAMPLE 10

1-[4-{2-(1,1-dimethylethylamino)-ethoxy}-phenyl]-3-[1H-indol-4-yl]-2-propen-1-one (E)

STEP A: 1-[4-(2-chloroethoxy)-phenyl]-ethanone

A mixture of 100 mg of 4-hydroxy-acetophenone, 96 mg of n-tetrabutylammonium acid sulfate, 1.5 ml of 50% sodium hydroxide solution, 3 ml of benzene, 1.5 ml of acetonitrile and 0.2 ml of 2-chloroethyl p-toluene sulfonate was refluxed for 18 hours under an inert atmosphere and the decanted phase was extracted with benzene. The organic phase was washed with water, dried over a deshydrant and evaporated to dryness under reduced pressure. The residue was chromatographed over silica and eluted with dichloroethane to obtain 127 mg of 1-[4-(2-chloroethoxy)-phenyl]-ethanone melting at ≃62° C.

STEP B: 1-[4-{-2-(1,1-dimethylethylamino)-ethoxy}-phenyl]-ethanone

A mixture of 6.5 g of the product of Step A in 30 ml of tert.-butylamine was heated at 120° C. for 30 hours and was then diluted with water and extracted with ethyl acetate. The organic phase was washed with water, dried over a deshydrant, filtered and evaporated to dryness. The residue was chromatographed over silica and eluted with a 9-1 ethyl acetate-triethylamine mixture to obtain 7.264 g of 1-[4-{-2-(1,1-dimethylethylamino)-ethoxy}-phenyl]-ethanone.

STEP C:
1-[4-{-2-(1,1-dimethylethylamino)-ethoxy}-phenyl]-3-[1H-indol-4-yl]-2-propen-1-one (E)

A mixture of 2.55 g of indole-4-carboxaldehyde and 4 ml of 50% sodium hydroxide solution was added with stirring under an inert atmosphere to a solution of 3.5 g of the product of Step B in 40 ml of ethanol and after stirring for 24 hours, the mixture was diluted with water and extracted with ethyl acetate. The organic phase was washed with water and the wash water was reextracted with an 8-2 chloroform-methanol mixture. The extract was washed with water and aqueous sodium chloride solution and the combined organic phases were dried over a deshydrant and were evaporated to dryness. The residue was chromatographed over silica gel and eluted with a 9-1 ethyl acetate-triethylamine mixture to obtain 4.3 g of 1-[4-{-2-(1,1-dimethylamino)-ethoxy}-phenyl]-3-[1H-indol-4-yl]-2-propen-1-one (E) melting at ≃162° C.

A solution of 1.043 g of oxalic acid dihydrate in 20 ml of methanol was added with stirring at 80° C. to a suspension of 3 g of the above free base in 40 ml of ethanol and 55 ml of methanol and the mixture was filtered. The filtrate was evaporated to dryness under reduced pressure and the residue was taken up in a hot mixture of 50 ml of methanol, 100 ml of ethanol and 100 ml of water and the hot mixture was filtered. The filtrate was concentrated and crystallization was begun. The mixture was filtered and the product was dried at 80° C. under reduced pressure to obtain 1.1 g of the neutral ethanedioate salt of the base melting at ≃248° C.

Analysis: $C_{23}H_{26}N_2O_2 \cdot \frac{1}{2}(C_2H_2O_4)$; molecular weight =407.494. Calcuated: %C 70.74, %H 6.68, %N 6.87. Found: %C 70.5, %H 6.8, %N 6.7.

EXAMPLE 11

1-[2-{3-(1,1-dimethylethylamino)-propoxy}-phenyl]-3-[1H-indol-4-yl]-1-propanone

Using the procedure of Example 2, 3.616 g of the base of Example 5 were reacted to obtain 2.98 g of 1-[2-{3-(1,1-dimethylethylamino)-propoxy}-phenyl]-3-[1H-indol-4-yl]-1-propanone melting at ≃64° C. 2 g of the product were dissolved in 30 ml of hot isopropanol and ethyl acetate containing hydrogen chloride was added thereto to obtain an acid pH. The mixture was iced and filtered and the product was dried at 80° C. under reduced pressure and crystallized from isopropanol to obtain 1.22 g of the hydrochdloride of the base melting at ≃162° C.

UV Spectrum (ethanol):

| | | | |
|---|---|---|---|
| Max. at 215 nm | $E_1^1 =$ 1278 | $\epsilon =$ | 53,000 |
| Max. at 251 nm | $E_1^1 =$ 257 | $\epsilon =$ | 10,700 |
| Max. at 270 nm | $E_1^1 =$ 198 | $\epsilon =$ | 8,200 |
| Max. at 278 nm | $E_1^1 =$ 192 | $\epsilon =$ | 7,950 |
| Infl. at 282 nm | $E_1^1 =$ 188 | | |
| Max. at 288 nm | $E_1^1 =$ 167 | $\epsilon =$ | 6,950 |
| Infl. at 301 nm | $E_1^1 =$ 92 | | |

EXAMPLE 12

Neutral (E) butenedioate salt of α-[2-{3-(1,1-dimethylethylamino)-propoxy}-phenyl]-1H-indol-4-propanol Using the procedure of Example 3, 2.937 g of the base of Example 11 was reacted to obtain 2.86 g of neutral (E) bentenedioate salt of α-[2-{3-(1,1-dimethylethylamino)-propoxy}-phenyl]-1H-indol-4-propanol melting at ≃240° C. after crystallization from methanol.

Analysis: $C_{24}H_{32}N_2O_2 \cdot \frac{1}{2}C_4H_4O_4$; molecular weight=438.571. Calculated: %C 71.21, %H 7.81, %N 6.39. Found: %C 71.1, %H 7.9, %N 6.4.

EXAMPLE 13

N-[2-{2-(3-[1H-indol-4-yl]-propyl)-phenoxy}-ethyl]-2-methyl-2-propanamine

Using the procedure of Example 4, the base of Example 1 was reacted for 6 hours to obtain N-[2-{2-(3-[1H-indol-4-yl]-propyl)phenoxy}-ethyl]-2-propanamine melting at ≃112° C. and having an Rf=0.39 (9-1 ethylacetate-triethylamine).

EXAMPLE 14

1-[2-{2-(1,1-dimethylamino)-ethoxy}-phenyl]-3-[1H-indol-4-yl]-1-propanone

STEP A:
3-(1H-indol-4-yl)-1-(2-hydroxyphenyl)-2-propen-1-one 0.5 ml of a 38% potassium hydroxide solution was added with stirring at 30° C. under an inert atmosphere to a mixture of 0.132 g of indol-4-carboaldehyde, 0.1 ml of 2-hydroxy-acetophenone and 0.189 g of triethylbenzyl ammonium chloride in 2 ml of ethanol and after stirring at 30° for 23 hours, the mixture was diluted with water and extracted with ethyl acetate. The organic phase was washed with water, dried over a deshydrant and evaporated to dryness. The residue was chromatographed over silica and eluted with methylene chloride to obtain 159 mg of 3-(1H-indol-4-yl)-1-(2-hydroxyphenyl)-2-propen-1-one melting at ≃164° C.

STEP B:
1-[2-hydroxy-phenyl]-3-[1H-indol-4-yl]-1-propanone

A mixture of 200 mg of the product of Step A in 10 ml of methanol was hydrogenated in the presence of palladized carbon until absorption ceased and was then filtered. Chromatography over silica and elution with a 6-3-1 cyclohexane-dichloromethane-triethylamine mixture yielded 143 mg of 1-[2-hydroxy-phenyl]-3-[1H-indol-4-yl]-1-propanone melting at 143° C.

UV Spectrum (ethanol):

| | | | |
|---|---|---|---|
| Max. at 214 nm | $E_1^1 =$ 2,080 | $\epsilon =$ | 55,200 |
| Max. at 254 nm | $E_1^1 =$ 555 | $\epsilon =$ | 14,700 |
| Infl. at 275 nm | $E_1^1 =$ 295 | | |
| Infl. at 286 nm | $E_1^1 =$ 220 | | |
| Max. at 323 nm | $E_1^1 =$ 117 | $\epsilon =$ | 4,700 |

STEP C:
1-[2-{2-(1,1-dimethylamino)-ethoxy}-phenyl]-3-[1H-indol-4-yl]-1-propanone A mixture of 2.7 g of the product of Step B in 50 ml of benzene was added with stirring under an inert atmosphere to 25 ml of acetonitrile and 345.5 mg of tetrabutylammonium acid sulfate and 39 ml of a 50% aqueous sodium hydroxide solution were added thereto. The mixture was heated to 80° C. and 1.47 g of dimethylaminoethyl chloride hydrochloride were added followed after 3 hours by 0.738 g of hydrochloride. The mixture was diluted with water and extracted with ethyl acetate. The decanted aqueous phase was reextracted with ethyl acetate and the combined organic phases were washed with water, dried over a deshydrant, filtered and evaporated to dryness. The residue was chromatographed over silica and eluted with a 6-3-1 chloroform-acetone-triethylamine mixture to obtain 2.81 g of 1-[2-{2-(1,1-dimethylamino)-ethoxy}-phenyl]-3-[1H-indol-4-yl]-1-propanone melting at 64° C.

UV Spectrum (ethanol):

| Max. at 216 nm | $E_1^1 =$ 1,589 | $\epsilon =$ 53,500 |
|---|---|---|
| Max. at 249 nm | $E_1^1 =$ 286 | $\epsilon =$ 9,600 |
| Max. at 270 nm | $E_1^1 =$ 250 | $\epsilon =$ 8,400 |
| Max. at 278 nm | $E_1^1 =$ 247 | $\epsilon =$ 8,300 |
| Max. at 289 nm | $E_1^1 =$ 213 | $\epsilon =$ 7,200 |
| Infl. at 301 nm | $E_1^1 =$ 109 | |

EXAMPLE 15

1-[2-{2-(1,1-dimethylamino)-ethoxy}-phenyl]-1H-indol-4-propanol

A solution of 2.43 g of the product of Example 14 in 60 ml of methanol was added with stirring over 10 minutes under an inert atmosphere to 0.820 g of sodium borohydride and water was added while cooling in an ice bath. The mixture was extracted with ethyl acetate and the organic phase was washed with water, dried over a deshydrant, filtered and evaporated to dryness to obtain 2.42 g of 1-[2-{2-(1,1-dimethylaminl)-ethoxy}-phenyl]-1H-indol-4-propanol.

UV Spectrum (ethanol):

| Max. at 218 nm | $E_1^1 =$ 1,308 | $\epsilon =$ 44,300 |
|---|---|---|
| Max. at 270 nm | $E_1^1 =$ 279 | $\epsilon =$ 9,450 |
| Infl. at 276 nm | $E_1^1 =$ 260 | |
| Max. at 288 nm | $E_1^1 =$ 139 | $\epsilon =$ 4,700 |

A solution of 0.795 g of DL tartaric acid in 30 ml of hot methanol were added to a solution of 1.8 g of the free base in 30 ml of methanol and crystallization was induced with cooling. The mixture was vacuum filtered and the product was crystallized from methanol to obtain 0.65 g of the tartrate salt of the free base melting at ≃170° C.

UV Spectrum (ethanol):

| Max. at 217 nm | $E_1^1 =$ 900 | $\epsilon =$ 44,000 |
|---|---|---|
| Max. at 269 nm | $E_1^1 =$ 187 | $\epsilon =$ 9,100 |
| Infl. at 274 nm | $E_1^1 =$ 175 | |
| Infl. at 281 nm | $E_1^1 =$ 138 | |
| Max. at 288 nm | $E_1^1 =$ 97 | $\epsilon =$ 4,750 |

EXAMPLE 16

1-[2-{2-dimethylamino-ethoxy}-phenyl]-3-[1H-indol-4-yl]-2-propen-1-one

A mixture of 3 g of the product of Step A of Example 14, 50 ml of benzene, 25 ml of acetonitrile and 387 mg of tetrabutylammonium acid sulfate was stirred under an inert atmosphere and 45 ml of 50% sodium hydroxide solution were added. The mixture was heated to 50° C. and 1.64 g of dimethylaminoethyl chloride hydrochloride were added and after 3 hours, 0.820 g of hydrochloride were formed. After 4 hours, the mixture was diluted with water and extracted with ethyl acetate. The decanted aqueous phase was reextracted with ethyl acetate and the combined organic phases were washed with water, dried over a deshydrant, filtered and evaporated to dryness. The residue was chromatographed over silica and eluted with a 6-3-1 chloroform-acetone-triethylamine mixture to obtain 3.7 g of 1-[2-{2-dimethylamino-ethoxy}-phenyl]-3-[1H-indol-4-yl]-2-propen-1-one UV Spectrum (ethanol):

| Max. at 216 nm | $E_1^1 =$ 870 | $\epsilon =$ 29,100 |
|---|---|---|
| Max. at 266 nm | $E_1^1 =$ 353 | $\epsilon =$ 11,800 |
| Infl. at 344 nm | $E_1^1 =$ 246 | |
| Max. at 387 nm | $E_1^1 =$ 380 | $\epsilon =$ 12,700 |

A solution of 0.819 g of oxalic acid dihydrate in 20 ml of methanol was added to a solution of 2.18 of the free base in 218 g of the free base in 40 ml of methanol and after the addition of 30 ml of isopropanol, the mixture was concentrated and crystallization induced with cooling. The mixture was filtered and the product was dried at 80° C. under reduced pressure to obtain 2 g of the acid oxalate salt of the said base melting at ≃174° C.

UV Spectrum (ethanol):

| Max. at 264 nm | $E_1^1 =$ 330 | $\epsilon =$ 14,007 |
|---|---|---|
| Infl. at 358 nm | $E_1^1 =$ 250 | |
| Max. at 390 nm | $E_1^1 =$ 354 | $\epsilon =$ 15,025 |

EXAMPLE 17

N,N-dimethyl-2-[2-{3-(1H-indol-4-yl)-propyl}-phenoxy]-ethanamine

A solution of 2.245 g of the base of Example 15 in 25 ml of tetrahydrofuran were added to 25 ml of liquid ammonia at −78° C. and 2 g of sodium pieces were added at −40° C. The mixture was stirred for one hour at −40° C. and 16 g of ammonium chloride were added at −40° C. The ammonia was slowly evaporated at room temperature and water was slowly added thereto. The mixture was extracted with ethyl acetate and the extract was washed with water, dried over a deshydrant, filtered and evaporated to dryness. The residue was chromatographed over silica and eluted with a 9-1 ethyl acetate-triethylamine mixture to obtain 1.9 g of N,N-dimethyl-2-[2-{3-(1H-indol-4-yl)-propyl}-phenoxy]-ethanamine melting at ≃78° C.

UV Spectrum (ethanol):

| Max. at 220 nm | $E_1^1 =$ 1,687 | $\epsilon =$ 54,400 |
|---|---|---|
| Max. at 271 nm | $E_1^1 =$ 375 | $\epsilon =$ 12,000 |
| Max. at 279 nm | $E_1^1 =$ 350 | $\epsilon =$ 11,300 |
| Max. at 289 nm | $E_1^1 =$ 192 | $\epsilon =$ 6,200 |

A solution of 0.780 g of DL tartaric acid in 30 ml of hot ethanol was added to a solution of 1.68 g of the above base in 40 ml of hot ethanol and the mixture was filtered. The product was crystallized from methanol to obtain 2.153 g of the acid tartrate salt of the said base melting at 190° C.

UV Spectrum (ethanol):

| Max. at 219 nm | $E_1^1 =$ 1,060 | $\epsilon =$ 50,100 |
|---|---|---|
| Infl. at 267 nm | $E_1^1 =$ 211 | |
| Max. at 270 nm | $E_1^1 =$ 225 | $\epsilon =$ 10,600 |
| Max. at 277 nm | $E_1^1 =$ 211 | $\epsilon =$ 10,000 |
| Max. at 289 nm | $E_1^1 =$ 119 | $\epsilon =$ 5,600 |

EXAMPLE 18

1-[2-{2-(1-piperidinyl)-ethoxy}-phenyl]-3-[1H-indol-4-yl]-1-propanone

Using the procedure of Example 14, Step C, 2-piperidino-1-chloro-ethane hydrochloride was reacted to obtain 1-[2-{2-(1-piperidinyl)-ethoxy}-phenyl]-3-[1H-indol-4-yl]-1-propanone melting at 78° C.

UV Spectrum (ethanol):

| | | |
|---|---|---|
| Max. at 215 nm | $E_1^1 = 1,454$ | $\epsilon = 54,700$ |
| Max. at 248 nm | $E_1^1 = 264$ | $\epsilon = 9,900$ |
| Max. at 268 nm | $E_1^1 = 225$ | $\epsilon = 8,500$ |
| Max. at 278 nm | $E_1^1 = 221$ | $\epsilon = 8,300$ |
| Infl. at 280 nm | $E_1^1 = 217$ | |
| Max. at 288 nm | $E_1^1 = 190$ | $\epsilon = 7,150$ |
| Infl. at 301 nm | $E_1^1 = 101$ | |

EXAMPLE 19

1-[2-{2-(1-piperidinyl)-ethoxy}-phenyl]-3-[1H-indol-4-yl]-2-propen-1-one

Using the procedure of Example 16, 2-piperidino-1-chloroethane hydrochloride was reacted to obtain 1-[2-{2-(1-piperidinyl)-ethoxy}-phenyl]-3-[1H-indol-4-yl]-2-propen-1-one. Its acid oxalate was prepared and melted at 174° C.

UV Spectrum (ethanol):

| | | |
|---|---|---|
| Max. at 265 nm | $E_1^1 = 297$ | $\epsilon = 13,800$ |
| Infl. at 345 nm | $E_1^1 = 195$ | |
| Max. at 390 nm | $E_1^1 = 319$ | $\epsilon = 14,800$ |

EXAMPLE 20

α-[2-{2-(1-piperidinyl)-ethoxy}-phenyl]-1H-indol-4-propanol

Using the procedure of Example 15, the product of Example 18 was reacted to obtain α-[2-{2-(1-piperidinyl)-ethoxy}-phenyl]-1H-indol-4-propanol. Its neutral fumarate salt was formed and melted at 190° C.

UV Spectrum (ethanol):

| | | |
|---|---|---|
| Max. at 218 nm | $E_1^1 = 1,190$ | $\epsilon = 52,000$ |
| Max. at 270 nm | $E_1^1 = 231$ | $\epsilon = 10,100$ |
| Infl. at 276 nm | $E_1^1 = 215$ | |
| Infl. at 281 nm | $E_1^1 = 180$ | |
| Infl. at 288 nm | $E_1^1 = 117$ | |

EXAMPLE 21

4-[3-{2-(2-[1-piperidinyl]-ethoxy)-phenyl}-propyl]-1H-indole

Using the procedure of Example 17, the product of Example 20 was reacted to obtain 4-[3-{2-(2-[1-piperidinyl]-ethoxy)-phenyl}-propyl]-1H-indole. Its acid tartrate salt was formed and melted at 125° C.

UV Spectrum (ethanol):

| | | |
|---|---|---|
| Max. at 217 nm | $E_1^1 = 818$ | $\epsilon = 41,900$ |
| Max. at 270 nm | $E_1^1 = 975$ | $\epsilon = 9,000$ |
| Max. at 276 nm | $E_1^1 = 166$ | $\epsilon = 8,500$ |
| Infl. at 282 nm | $E_1^1 = 125$ | |
| Max. at 288 nm | $E_1^1 = 93$ | $\epsilon = 4,750$ |

EXAMPLE 22

1-[2-{2-(bis-[isopropyl]amino)-ethoxy}-phenyl]-1H-indol-4-yl]-1-propanone

Using the procedure of Example 14, Step C, diisopropylaminoethyl chloride hydrochloride was reacted to obtain 1-[2-{2-(bis-[isopropyl]amino)-ethoxy}-phenyl]-1H-indol-4-yl]-1-propanone.

UV Spectrum (ethanol):

| | | |
|---|---|---|
| Max. at 214 nm | $E_1^1 = 1,292$ | $\epsilon = 50,700$ |
| Max. at 249 nm | $E_1^1 = 239$ | $\epsilon = 9,400$ |
| Max. at 270 nm | $E_1^1 = 201$ | $\epsilon = 7,900$ |
| Max. at 279 nm | $E_1^1 = 199$ | $\epsilon = 7,800$ |
| Max. at 290 nm | $E_1^1 = 170$ | $\epsilon = 6,700$ |
| Infl. at 301 nm | $E_1^1 = 88$ | $\epsilon = 3,450$ |

EXAMPLE 23

1-[2-{2-(bis[isopropyl]-amino)-ethoxy}-phenyl]-3-[1H-indol-4-yl]-2-propen-1-one Using the procedure of Example 16, diisopropylamino ethyl chloride hydrochloride was reacted to obtain 1-[2{-2-(bis[isopropyl]-amino)-ethoxy}-phenyl]-3[1H-indol-4-yl]-2-propen-1-one. Its acid oxalate was prepared.

UV Spectrum (ethanol):

| | | |
|---|---|---|
| Infl. at 213 nm | $E_1^1 = 685$ | |
| Max. at 266–267 nm | $E_1^1 = 272$ | $\epsilon = 13,000$ |
| Infl. at 342 nm | $E_1^1 = 159$ | |
| Max. at 393 nm | $E_1^1 = 293$ | $\epsilon = 14,000$ |

EXAMPLE 24

α-[2-{2-(bis[isopropyl]amino)-ethoxy}-phenyl]-1H-indol-4-propanol

Using the procedure of Example 15, the product of Example 22 was reacted to obtain α-[2-{2-(bis[isopropyl]amino)-ethoxy}-phenyl]-1H-indol-4-propanol. Its benzoate was formed and it melted at ≃110° C.

UV Spectrum (ethanol):

| | | |
|---|---|---|
| Max. at 220 nm | $E_1^1 = 1,136$ | $\epsilon = 58,700$ |
| Infl. at 267 nm | $E_1^1 = 205$ | |
| Max. at 270 nm | $E_1^1 = 216$ | $\epsilon = 11,200$ |
| Infl. at 276 nm | $E_1^1 = 200$ | |
| Max. at 289 nm | $E_1^1 = 104$ | $\epsilon = 5,400$ |

EXAMPLE 25

N-[2-{2-(3-[1H-indol-4-yl]-propyl)}-phenoxy-ethyl]-N-isopropyl-2-propanamine Using the procedure of Example 17, the product of Example 24 was reacted to obtain N-[2-{2-(3-[1H-indol-4-yl]-propyl)}-phenoxyethyl]-N-isopropyl-2-propanamine. Its acid oxalate was formed and it melted at ≃108°–112° C.

UV Spectrum (ethanol):

| | | |
|---|---|---|
| Max. at 220 nm | $E_1^1 = 938$ | $\epsilon = 44,000$ |
| Max. at 270 nm | $E_1^1 = 198$ | $\epsilon = 9,300$ |
| Max. at 277 nm | $E_1^1 = 187$ | $\epsilon = 8,800$ |
| Max. at 289 nm | $E_1^1 = 106$ | $\epsilon = 5,000$ |

EXAMPLE 26

1,3-dihydro-4-[3-{2-(2-(1,1-dimethylethyl]-amino)-ethoxy}-phenyl]-propyl-2H-indol-2-one

STEP A:
N-[2-{2-(3-[3-chloro-1H-indol-4-yl]-propyl)-phenoxy}-ethyl]-2-methyl-2-propanamine A solution of 4.74 g of the product of Example 9 in 43 ml of acetic acid was added with stirring under an inert atmosphere to 2.17 g of N-chlorosuccinimide over 40 minutes and the mixture was diluted with water and iced. The mixture was made alkaline by addition of 32% sodium hydroxide solution and was extracted with ethyl acetate. The organic phase was washed with water, dried over a deshydrant, filtered and evaporated to dryness. The residue was chromatographed over silica and eluted with a 9-1 ethyl acetate-triethylamine mixture to obtain 3.76 g of N-[2-{2-(3-[3-chloro-1H-indol-4-yl]-propyl)-phenoxy}-ethyl]-2-methyl-2-propanamine.

STEP B:
1,3-dihydro-4-[3-(2-{2-[1,1-dimethylethylamino]-ethoxy}-phenyl)-propyl]-2H-indol-2-one A mixture of 3.76 g of the product of Step A in 94 ml of 94% ethanol and 94 ml of aqueous N hydrochloric acid was stirred under an inert atmosphere for 19 hours and was diluted with water and iced. The mixture was made alkaline by addition of 32% sodium hydroxide solution and was extracted with ethyl acetate. The organic phase was washed with water, dried over a deshydrant, filtered and evaporated to dryness. The residue was chromatographed over silica and eluted with a 9-1 ethyl acetate-triethylamine mixture to obtain 2.18 g of 1,3-dihydro-4-[3-(2-{2-[1,1-dimethylethylamino]-ethoxy}-phenyl)-propyl]-2H-indol-2-one.

A solution of the said free base in 10 ml of hot isopropanol was admixed with 0.690 g of fumaric acid and the mixture was iced and filtered. The product was dried and crystallized from a 1-7 methanol-isopropanol mixture to obtain 1.77 g of the neutral fumarate salt of the base melting at $\simeq 193°$ C.

UV Spectrum (ethanol):

| | | |
|---|---|---|
| Infl. at 216 nm | $E_1^1 = 769$ | |
| Infl. at 247 nm | $E_1^1 = 219$ | |
| Max. at 250 nm | $E_1^1 = 225$ | $\epsilon = 9,600$ |
| Infl. at 259 nm | $E_1^1 = 174$ | |
| Infl. at 269 nm | $E_1^1 = 93$ | |
| Max. at 276 nm | $E_1^1 = 79$ | $\epsilon = 3,350$ |
| Infl. at 288 nm | $E_1^1 = 30$ | |

EXAMPLE 27

1,3-dihydro-4-[3-{2-(3-[1,1-dimethylethylamino]-propoxy)-phenyl}-propyl]-2H-indol-2-one Using the procedure of Example 26, the product of Example 7 was reacted to obtain 1,3-dihydro-4-[3-{2-(3-[1,1-dimethylethylamino]-propoxy)-phenyl}-propyl]-2H-indol-2-one. Its neutral fumarate salt was formed and it melted at 223° C.

EXAMPLE 28

Preparation of 2-[3-(1H-indol-4-yl)propyl]phenol 22.6 ml of hydrazine hydrate were slowly added with stirring to 50 ml of diethyleneglycol and then 11.6 g of the product of Step B of Example 14 were added with stirring. 20 ml of 38% sodium hydroxide solution were added and the mixture was heated at 140° C. under an inert atmosphere for 30 minutes. The water was distilled followed by excess hydrazine hydrate at 210° C. The mixture was stirred for two hours and was cooled in an ice bath. Water was added and the mixture was extracted with ethyl acetate. The organic phase was washed with water, dried over a deshydratant, filtered and evaporated to dryness. The residue was chromatographed over silica and eluted with methylene chloride to obtain 8.613 g of 2-[3-(1H-indol4-yl)propyl]phenol melting at $\simeq 89°$ C.

UV Spectrum (ethanol):

| | | |
|---|---|---|
| Max. at 219 nm | $E_1^1 = 1,705$ | $\epsilon = 42900$ |
| Infl. at 260 nm | $E_1^1 = 313$ | |
| Max. at 273 nm | $E_1^1 = 380$ | $\epsilon = 9,550$ |
| Infl. at 278 nm | $E_1^1 = 375$ | |
| Max. at 289 nm | $E_1^1 = 225$ | $\epsilon = 5,650$ |
| Infl. at 310 nm | | |
| Infl. at 334 nm | | |

EXAMPLE 29

Tablets were prepared containing 100 mg of the neutral fumarate of N-[2-{2-(3-[1H-indol-4-yl]-propyl)-phenoxy}-ethyl]-2-methyl-2-propanamine or 1-[2-{2-(1,1-dimethylethylamino)-ethoxy}-phenyl]-3-[1H-indol-4-yl]-1-propanone hydrochloride or the acid oxalate of N-[2{-2-(3-[1H-indol-4-yl]-propyl)-phenoxy}-ethyl]-N-isopropyl-2-propanamine or the 1-[2-{3-(1,1-dimethylethylamino)propoxy}phenyl]3-(1H-indol-4yl)1-propanone hydrochloride and sufficient excipient of lactose, starch, talc and magnesium stearate for a final weight of 150 mg.

PHARMACOLOGICAL STUDY

A. Antiarythmic activity in rats

Male rats weighing about 300–350 g anesthestized by intraperitoneal administration of 1.20 g/kg of urethane were tracheotomized and an artifical respiration of 40 to 50 insufflations of 3 ml/minute were induced. Needles were implanted under the skin to register the electrocardiograms of the rats by derivation signal DII. The test products were administered orally or intraveinously and 5 minutes later, the jugular vein of the rats were perfused with 10 μg per minute or 0.2 ml of a solution of aconitine. The time for appearance of cardiac rhythm troubles was noted and the results were expressed as a percentage of increase of the time for appearance of cardiac rythm troubles as compared to the controls and as a function of the dose of the tested compounds. The results are reported in the following Table.

TABLE

| Product of Example | Method of Administration | Dose in mg/kg | % of increase in time |
|---|---|---|---|
| 1 | IV | 0.5 kg | 26 |
| | PO | 10 kg | 41 |
| 2 | IV | 2.5 kg | 40 |
| | PO | 25 kg | 32 |
| 3 | IV | 0.05 kg | 36 |
| | PO | 5 kg | 38 |
| 5 | IV | 2.5 kg | 56 |
| | PO | 2.5 kg | 41 |
| 9 | IV | 2.5 mg | 49 |
| | PO | 25 mg | 40 |
| 11 | IV | 1 mg | 42 |
| | PO | 25 mg | 66 |
| 20 | IV | 2.5 mg | 50 |

TABLE-continued

| Product of Example | Method of Administration | Dose in mg/kg | % of increase in time |
|---|---|---|---|
| 24 | IV | 0.25 mg | 25 |
|  | PO | 5 mg | 46.5 |
| 26 | IV | 1 mg | 25.5 |
| 28 | IV | 0.25 mg | 24 |

The results of the Table show that the compounds of the invention have a remarkable antiarythmic activity.

B. Anticalcic activity in vitro

The rat caudal arteries disengaged in spiral were joined to tension catches and were maintained in vats with 25 ml of buffered Krebs-sodium bicarbonate solution (120.8 mMNaCl; 5.9 mM of KCl; 1.2 mM $MgCl_2$; 1.2 mM $NaH_2PO_4$; 15.5 mM $NaHCO_3$; 12.6 mM glucose) at 37° C. saturated with a mixture of 95% oxygen and 5% carbon dioxide. The preparations were depolarized with a buffered solution to a concentration of 100 mM of potassium ions (26.7 mM NaCl; 100 mM of KCl; 1.2 mM of $MgCl_2$; 1.2 mM of $NaH_2PO_4$; 15.5 mM of $NaHCO_3$; 12.6 mM of glucose). 2.5 mM of calcium chloride in a volume of 250 μl were added thereto and the induced arterial contractions were determined. The operation was repeated every 15 minutes and each contraction was followed by two washings with a calcium free buffered solution. When a stable response was obtained, the operation was renewed in the presence of increasing concentration of the test product and the time of contact for each concentration was 15 minutes.

The arterial contractions was dependent on the entry of calcium ions into smooth muscle cells and are provoked by depolarization of the cells by potassium ions and by the action of noradrenaline liberated by presynaptic level. After the suppression of vasoconstrictrary action of noradrenaline, the tests were effected in the presence of $10^{-5}M$ of phentolamine, an α-adrenergic antagonist. The results were expressed in $CI_{50}$ or the amount of test compound inhibiting by 50% the contraction due to potassium ions and are reported in the following Table.

TABLE

| Product of Example | $CI_{50}$ in μM |
|---|---|
| 1 | 1.9 |
| 2 | 0.8 |
| 3 | 1.9 |
| 5 | 1.4 |
| 7 | 0.9 |
| 9 | 0.8 |
| 11 | 0.26 |
| 17 | 1.2 |
| 19 | 1.5 |
| 20 | 0.71 |
| 21 | 0.52 |
| 24 | 1.3 |
| 25 | 0.23 |

The results of the Table shows that the compounds of the invention have a strong anticalcic activity.

C. Acute toxicity

The $LD_0$ dose or the maximum amount of test compound orally administered to mice which did not kill any mice for 8 days was determined and the results are reported in the following Table.

TABLE

| Product of Example | $DL_O$ in mg/kg |
|---|---|
| 1 | >400 |
| 2 | 200 |
| 3 | 10 |
| 5 | 200 |
| 7 | 200 |
| 9 | 200 |
| 11 | 200 |
| 15 | 100 |
| 16 | 80 |
| 17 | >400 |
| 19 | >200 |
| 20 | 80 |
| 21 | 200 |
| 23 | 200 |
| 24 | 40 |
| 25 | 200 |
| 26 | 100 |

Various modifications of the compounds and method of the invention may be made without departing from the spirit or scope thereof and it is to be understood that the invention is intended to be limited only as defined in the appended claims.

What is claimed is:

1. A compound selected from the group consisting of 4-phenyl propyl-indoles of the formula

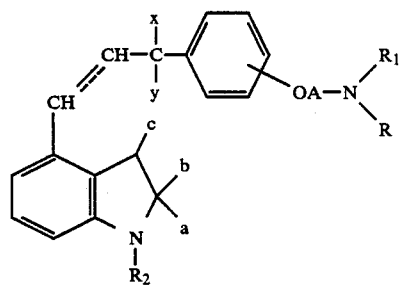

wherein R and $R_1$ are individually selected from the group consisting of hydrogen, linear alkyl of 1 to 5 carbon atoms, branched alkyl of 3 to 5 carbon atoms, cycloalkyl of 3 to 7 carbon atoms, cycloalkylalkyl of 4 to 7 carbon atoms and aralkyl of 7 to 12 carbon atoms optionally substituted with 1 to 3 members of the group consisting of halogen, methyl, ethyl, methoxy, ethoxy, $CF_3$—, $CH_3S$—, —$NH_2$ and —$NO_2$ or $R_1$ and R taken together with the nitrogen atom form an heterocycle selected from the group consisting of pyrrolidino, piperidino, morpholino and piperazinyl optionally substituted with a member of the group consisting of alkyl of 1 to 5 carbon atoms, phenyl, naphthyl and aralkyl of 7 to 12 carbon atoms, a together with b forms =O or a together with c forms a carbon-carbon bond, b is hydrogen or with a forms =O, c is hydrogen or with a forms a carbon-carbon bond, the dotted line is an optional carbon-carbon bond, A is —$(CH_2)_n$—, n is an integer from 2 to 5, $R_2$ is selected from the group consisting of hydrogen, linear alkyl of 1 to 5 carbon atoms and branched alkyl of 3 to 5 carbon atoms, x is hydrogen or —OH or together with y forms =O and y is hydrogen or together with x forms =O and their non-toxic, pharmaceutically acceptable acid addition salts.

2. A compound of claim 1 wherein a and c form a carbon-carbon bond.

3. A compound of claim 2 wherein $R_1$ and $R_2$ are both hydrogen.

4. A compound of claim 1 selected from the group consisting of N-[2-{2-(3-[1H-indol-4-yl]-propyl)-phenoxy}-ethyl]-2-methyl-2-propanamine and its non-toxic, pharmaceutically acceptable acid addition salts.

5. A compound of claim 1 selected from the group consisting of 1-[2-{3-(1,1-dimethylethylamino)-propoxy}-phenyl]-3-[1H-indol-4-yl]-1-propanone and its non-toxic, pharmaceutically acceptable acid addition salts.

6. A compound of claim 1 selected from the group consisting of N-[2-(2-{3-[1H-indol-4-yl]-propyl)-phenoxy}-ethyl]-N-isopropyl-2-propanamine and its non-toxic, pharmaceutically acceptable acid addition salts.

7. An antiarythmic composition comprising an antiarythmically effective amount of at least one compound of claim 1 and an inert pharmaceutical carrier.

8. A composition of claim 7 wherein in the compound a and c form a carbon-carbon bond.

9. A composition of claim 8 wherein in the compound $R_1$ and $R_2$ are both hydrogen.

10. A composition of claim 7 wherein the active compound is N-[2-{2-(3-[1H-indol-4-yl]-propyl)-phenoxy}-ethyl]-2-methyl-2-propanamine and its non-toxic, pharmaceutically acceptable acid addition salts.

11. A composition of claim 7 wherein the active compound is 1-[2-{3-(1,1-dimethylethylamino)-propoxy}-phenyl]-3-[1H-indol-4-yl]-1-propanone and its non-toxic, pharmaceutically acceptable acid addition salts.

12. A composition of claim 7 wherein the active compound is N-[2-(2-{3-[1H-indol-4-yl]-propyl)-phenoxy}-ethyl]-N-isopropyl-2-propanamine and its non-toxic, pharmaceutically acceptable acid addition salts.

13. A method of inducing antiarythmic activity in warm-blooded animals comprising administering to warm-blooded animals an antiarythmically effective amount of at least one compound of claim 1.

14. A method of claim 13 wherein in the active compound a and c form a carbon-carbon bond.

15. A method of claim 14 wherein in the active compound $R_1$ and $R_2$ are both hydrogen.

16. A method of claim 13 wherein the active compound is selected from the group consisting of N-[2-{2-(3-[1H-indol-4-yl]-propyl)-phenoxy}-ethyl]-2-methyl-2-propanamine and its non-toxic, pharmaceutically acceptable acid addition salts.

17. A method of claim 13 wherein the active compound is selected from the group consisting of 1-[2-{3-(1,1-dimethylethylamino)-propoxy}-phenyl]-3-[1H-indol-4-yl]-1-propanone and its non-toxic, pharmaceutically acceptable acid addition salts.

18. A method of claim 13 wherein the active compound is selected from the group consisting of N-[2-(2-{3-[1H-indol-4-yl]-propyl)-phenoxy}-ethyl]-N-isopropyl-2-propanamine and its non-toxic, pharmaceutically acceptable acid addition salts.

* * * * *